United States Patent
Marriott et al.

(10) Patent No.: US 8,465,792 B2
(45) Date of Patent: Jun. 18, 2013

(54) MONITOR SYSTEM FOR COATING APPARATUS

(75) Inventors: Douglas Marriott, Hamilton (CA); Robert Eric Mueller, Milton (CA)

(73) Assignee: Arcelormittal Dofasco, Inc. (CA)

( * ) Notice: Subject to any disclaimer, the term of this patent is extended or adjusted under 35 U.S.C. 154(b) by 961 days.

(21) Appl. No.: 11/620,379

(22) Filed: Jan. 5, 2007

(65) Prior Publication Data

US 2007/0128344 A1    Jun. 7, 2007

Related U.S. Application Data

(63) Continuation of application No. PCT/CA2005/001123, filed on Jul. 18, 2005.

(60) Provisional application No. 60/588,356, filed on Jul. 16, 2004.

(51) Int. Cl.
*C23C 14/54* (2006.01)

(52) U.S. Cl.
USPC ............ 427/9; 118/313; 118/688; 427/421.1

(58) Field of Classification Search
USPC .................. 427/8–10, 421.1–427.7; 118/300, 118/313, 314, 663, 665, 667, 668, 679, 688, 118/689, 690, 712, 713, 714
See application file for complete search history.

(56) References Cited

U.S. PATENT DOCUMENTS

| | | | |
|---|---|---|---|
| 4,876,458 A | 10/1989 | Takeda et al. | |
| 5,312,039 A | 5/1994 | Sayka et al. | |
| 5,778,724 A * | 7/1998 | Clapp et al. | 73/159 |
| 5,986,277 A | 11/1999 | Bourque et al. | |
| 6,023,367 A * | 2/2000 | Kurtz | 359/362 |
| 6,049,382 A * | 4/2000 | Lazaro Gomez | 356/336 |
| 6,157,756 A * | 12/2000 | Ishiwata | 385/31 |
| 6,785,400 B1 * | 8/2004 | Farina | 382/100 |
| 2002/0109112 A1 * | 8/2002 | Guha et al. | 250/559.46 |
| 2005/0073437 A1 * | 4/2005 | Perri | 340/944 |

FOREIGN PATENT DOCUMENTS

| | | |
|---|---|---|
| JP | 54-112751 A | 9/1979 |
| JP | 01-159086 A | 6/1989 |
| JP | 03-186382 A | 8/1991 |

(Continued)

OTHER PUBLICATIONS

Antonakos, James. "Image Processing Fundamentals Part 2: Math, Math, Math", Circuit Cellar Online #137, Dec. 2001.*

*Primary Examiner* — Michael Cleveland
*Assistant Examiner* — Alexander Weddle
(74) *Attorney, Agent, or Firm* — Steven Greenberg; Carey Rodriguez Greenberg O'Keefe, LLP

(57) ABSTRACT

A spray monitoring device analyzes images obtained from a beam passing through a spray pattern applying a spray to a substrate, and identifies discontinuities in the image as indicative of a discontinuity in a spray pattern. The spray pattern is produced by a plurality of nozzles spaced apart across the substrate for applying a suitable coating thereto. The beam is produced by a laser, that preferably has a collimator for distributing the beam intensity. The beam is imaged by a camera that provides a constant image to a computers where the scattering of beam light by the spray pattern is processed by image processing software and optionally provided to a user interface for analysis. Discontinuities detected by the user or software indicate faulty spray nozzles and may trigger remedial action.

11 Claims, 4 Drawing Sheets

FOREIGN PATENT DOCUMENTS

| | | |
|---|---|---|
| JP | 03-291510 A | 12/1991 |
| JP | 05-031409 A | 2/1993 |
| JP | 09-113231 A | 5/1997 |
| JP | 2000-019057 A | 1/2000 |

* cited by examiner

MONITOR SYSTEM FOR COATING APPARATUS

This is a continuation of PCT Application No. PCT/CA2005/001123 filed on Jul. 18, 2005 designating the U.S.A., which claims priority from U.S. Patent Application No. 60/588,356 filed on Jul. 16, 2004.

FIELD OF THE INVENTION

The present invention relates to apparatus and methods of monitoring the application of a fluid to a substrate.

BACKGROUND

It is frequently necessary to coat a substrate with a fluid during a manufacturing process. The application of the coatings may be for protective purposes or as part of the manufacturing process, and it is frequently essential that the fluid be applied in a uniform manner. Many manufacturing processes produce a substrate in a continuous manner as a web, and require the coating to be applied to the web as it is produced. A typical application for such coating is in the steel industry where an oil based lubricant is applied to a moving metal strip. The lubricant is required to assist in the further processing of the steel strip, and, accordingly, the film thickness of the lubricant must be uniform. Failure to provide a uniform coating will lead to inconsistencies in the further manufacturing process and the possibility of damage to the manufacturing equipment.

The coating is frequently applied through an array of spray nozzles positioned in the path of the substrate. Each of the spray heads has a number of nozzles that in ideal circumstances will produce a uniform spray pattern and distribute the sprayed fluid evenly. There is a possibility that the nozzles may become blocked or experience wear, which can produce an uneven spray pattern, and consequently an uneven coating. When such a defect is discovered, it may be necessary to call back significant quantities of material that have been processed with a possibly defective coating. Therefore, the efficacy of the coating is typically inspected periodically, but usually by manual observation. This is both time consuming and inconsistent, and requires significant skill on the part of the operator to recognize the existence of a fault.

It is therefore an object of the present invention to provide a method and apparatus in which the above disadvantages are obviated or mitigated.

SUMMARY OF THE INVENTION

In general terms, the present invention provides a system or method in which a coherent light source, typically a laser, is directed through a spray pattern. A camera is positioned to record the image of a beam as it propagates through the spray pattern and analyze the image to determine spray uniformity and continuity of the spray pattern.

Preferably the camera is integrated with the control system for the apparatus to provide an indication of inconsistent spraying and initiate remedial action.

In one aspect, the present invention provides a method of monitoring the application of coating to a substrate from a plurality of nozzles spaced apart across the substrate. The method comprises the steps of projecting a beam of coherent radiation through a spray of coating from said nozzles, obtaining an image of the beam as it propagates through the spray, and processing the image to determine variations in a characteristic indicative of the presence of the spray.

In another aspect, the present invention provides a system for monitoring the application of coating to a surface of a substrate, the coating being applied as a spray from a plurality of nozzles spaced apart across the substrate. The system comprises a coherent radiation source arranged to direct a beam of coherent radiation through the spray; an imaging device for obtaining an image of the beam as it propagates through the spray; and a computing device having a processor and being connected to the imaging device, the processor executing image processing software to process the image in order to determine variations in a characteristic indicative of the presence of the spray.

In yet another aspect, the present invention provides an apparatus for monitoring the application of coating to a substrate, the coating being applied by a plurality of nozzles spaced apart across the substrate. The apparatus comprises a coating station having a feeder for continuously feeding the substrate through the apparatus; at least one sprayhead connected to the coating station and positioned a predetermined distance from the substrate, the sprayhead having a plurality of nozzles, the nozzles being connected to a source of coating to enable coating to be fed through the nozzles to produce a spray of coating, the spray of coating being applied to a surface of the substrate; at least one coherent radiation source arranged to direct a beam of coherent radiation through the spray as it is applied to the substrate; an imaging device for obtaining an image of the beam as it propagates through the spray; and a computing device having a processor for processing the image to determine variations in a characteristic indicative of the presence of the spray.

BRIEF DESCRIPTION OF THE DRAWINGS

An embodiment of the invention will now be described by way of example only with reference to the accompanying drawings in which.

DETAILED DESCRIPTION OF THE INVENTION

Figure 1:
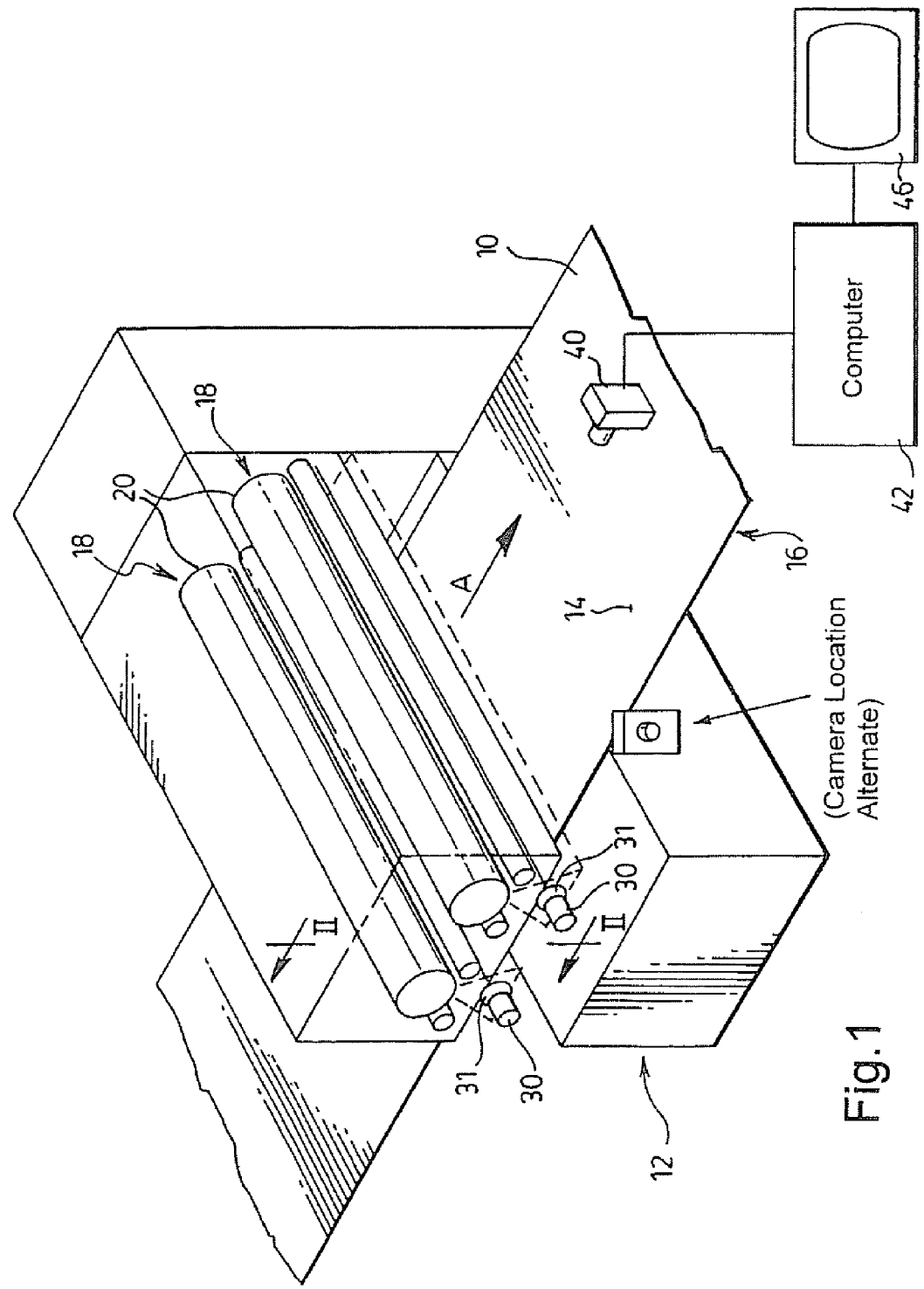
FIG. 1 is a perspective view of a coating apparatus.

Referring therefore to FIG. 1, a substrate 10, for example a steel strip, is passed through a coating station 12 to obtain a coating from a fluid lubricant on one or both of oppositely directed surfaces 14, 16. In the embodiment shown in FIG. 1, the coating station 12 includes sprayheads 18 arranged on opposite sides of the substrate 10 (only the upper sprayheads 18 are visible in FIG. 1), although coating on only one side may be utilised where appropriate. A pair of sprayheads 18 are located at longitudinally spaced locations in the direction of movement of the substrate indicated by arrow A to provide successive coatings.

Figure 2:
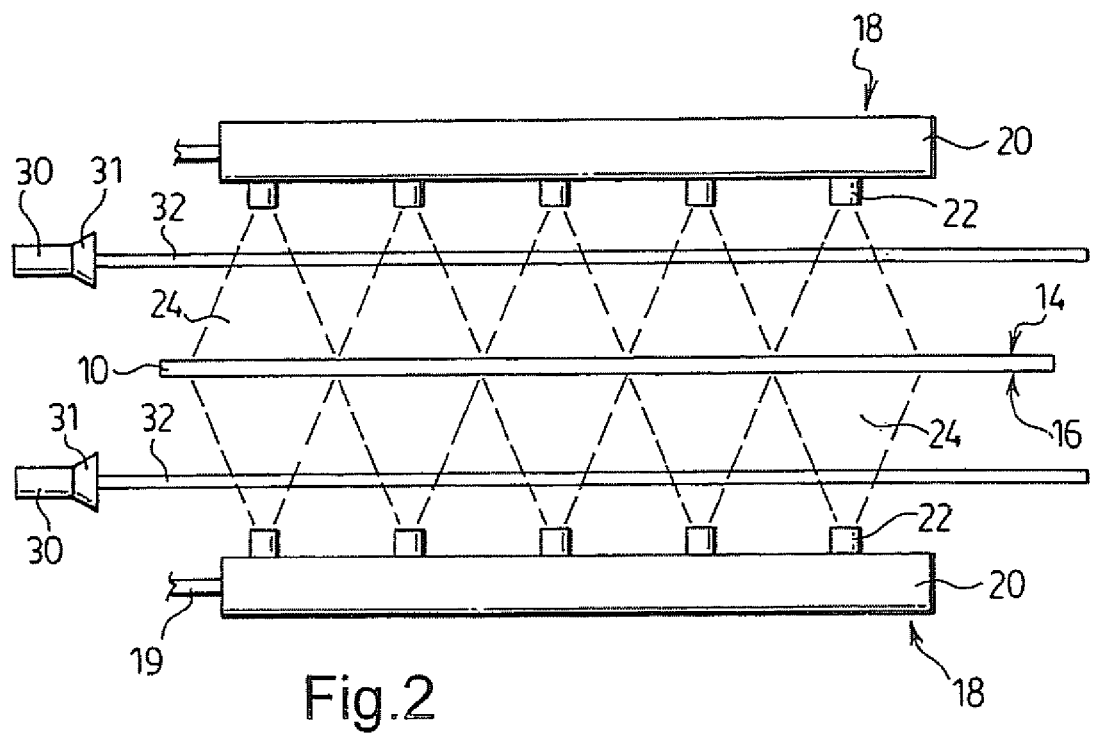
FIG. 2 is a view on the line II-II of FIG. 1.

As can best be seen in FIG. 2, each of the sprayheads 18 includes a manifold 20 connected to a pressurized supply 19 of fluid to be applied to the surfaces 14, 16. A series of nozzles 22 are connected to the manifold 20 and each produce a generally conical spray pattern 24. The form of the nozzles 22 is well known and need not be described in further detail. The nozzles 22 are spaced apart along the manifold 20, and thus across the width of the substrate 10 creating a fluid plume, to produce a substantially uniform distribution of the coating fluid to the respective one of the surfaces 14, 16 of the substrate 10.

To monitor the uniformity of coating produced by the sprayheads 185 a laser 30 is located to the same side of the substrate as the manifold 20 that is being monitored. The laser 30 produces a beam 32 of coherent radiation of a particular wavelength, preferably in the direction parallel to the axis of the manifold 20. The laser 30 is positioned such that the beam 32 passes through the overlapping spray patterns 24. Where a plurality of sprayheads 18 are utilized as shown in FIG. 1, each of the sprayheads 18 has an associated laser 30. A suitable laser 30 is one of the SNF Series lasers available under the trademark LASIRIS™.

Preferably, the beam 32 is a non-Gaussian, uniform line, produced by a collimated line head 31. A suitable collimated line head is also available under the trademark LASIRIS™. Particularly, model C-25 has shown particularly favourable results, having a collimated line length of 25 mm. However, model C-48 (48 mm line length) is also suitable. It will be appreciated that other line lengths may be used depending on the availability of components. A collimated beam 32 is beneficial as the collimator 31 transforms the traditional laser "dot" into a uniform intensity line, which retains a substantially uniform intensity across the beam width. This can be contrasted with the traditional Gaussian beam intensity distribution that has a central "hotspot" and where the intensity weakens towards the beam edges. Moreover, a collimator 31 is ideal for applications requiring a wide range of working distances. However, a traditional Gaussian beam may also be used if desired.

A camera 40 (FIG. 1) is positioned so as to be able to image the spray pattern 24 from the manifolds 20. Where practical, the camera 40 is located above the substrate with a field of view in the direction of motion of the substrate 10. Where this is impractical due to processing considerations, a camera 40 may be disposed to one side of the coating station but spaced from the lasers 30 so as to have a field of view including each spray pattern 24 from the respective sprayheads 18 (see "alternate location" in FIG. 1). Where multiple beams 32 are to be imaged, the camera 40 is positioned out of the horizontal plane passing through the manifolds 20. Typically a displacement of 5 cm to either side of the plane is sufficient to enable each beam to be imaged. Alternatively, the lasers 30 may be staggered in the vertical direction so that the respective beams 32 are vertically offset. Where manifolds 20 are located on both sides of the substrate 10 as shown in FIG. 2, a camera 40 is required on each side in order to image the respective spray patterns.

The camera 40 provides a continuous image to an image processing computer 42 located either within the camera 40 or remotely from the coating apparatus 12. The images obtained by the camera 40 may be processed such as by a narrow band optical filter (not shown) to enhance the contrast between the image produced by the beam 32 and the background The 28 computer 42 processes the images and produces an output to a user interface 46, from which the uniformity of the plume can be determined. The output may be either a pass/fail signal and/or an image that can be viewed by the operator, as shown in more detail in FIG. 4.

Figure 3:
FIG. 3 is a representation of images obtained from the apparatus of FIG. 1 under different operating conditions.
Figure 3:
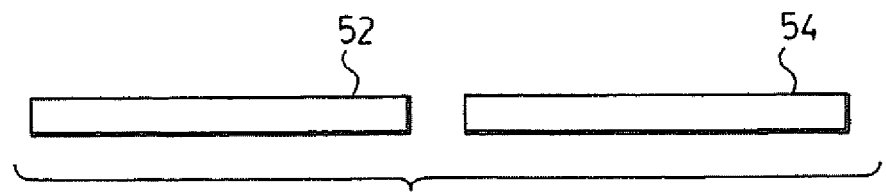

In operation, the beam 32 is propagated through the spray patterns 24, and with each of the nozzles 22 functioning correctly, will be uniformly scattered as the beam 32 is propagated. The scattering is induced by the physical characteristics of the spray pattern 24 and the resultant scattering will be viewed by the camera 40 as a bright horizontal band 50 as indicated in FIG. 3(a).

The collimator 31 collimates the beam 32, to provide a uniform intensity line. The uniform beam width is useful because regardless of where the plume crosses the beam 32 the incident light intensity, and thus the scattered light intensity, is substantially constant. This substantially constant scattering facilitates the setting of detection thresholds in the camera 40 and computer 42 for monitoring the spray patterns 24 and plume. A standard beam having a Gaussian intensity distribution may be used but it is sensitive to alignment. If the plume wanders off the axis of the laser beam 32, the incident light intensity drops off This can lead to increased error in detecting disruptions in the spray pattern 24.

The camera 40 therefore obtains images and checks the images for the presence of such a horizontal band 50. As will be described in more detail below with reference to FIG. 5, the image processing isolates the horizontal band 50 and determines the uniformity of the intensity along the horizontal extent of the sprayheads 18. Discontinuities in the image are indicative of discontinuities on the sprayhead and therefore these may be monitored and correlated with malfunction of the nozzles 22.

Wherever discontinuity is detected, remedial action may be taken and the uniformity of the spraying restored.

The image obtained from the camera 40 is formed from a matrix of pixels each having a discrete value associated with the intensity of the pixel. This format of image allows information on the spray pattern 24 to be extracted and utilized in the production process.

Figure 4:
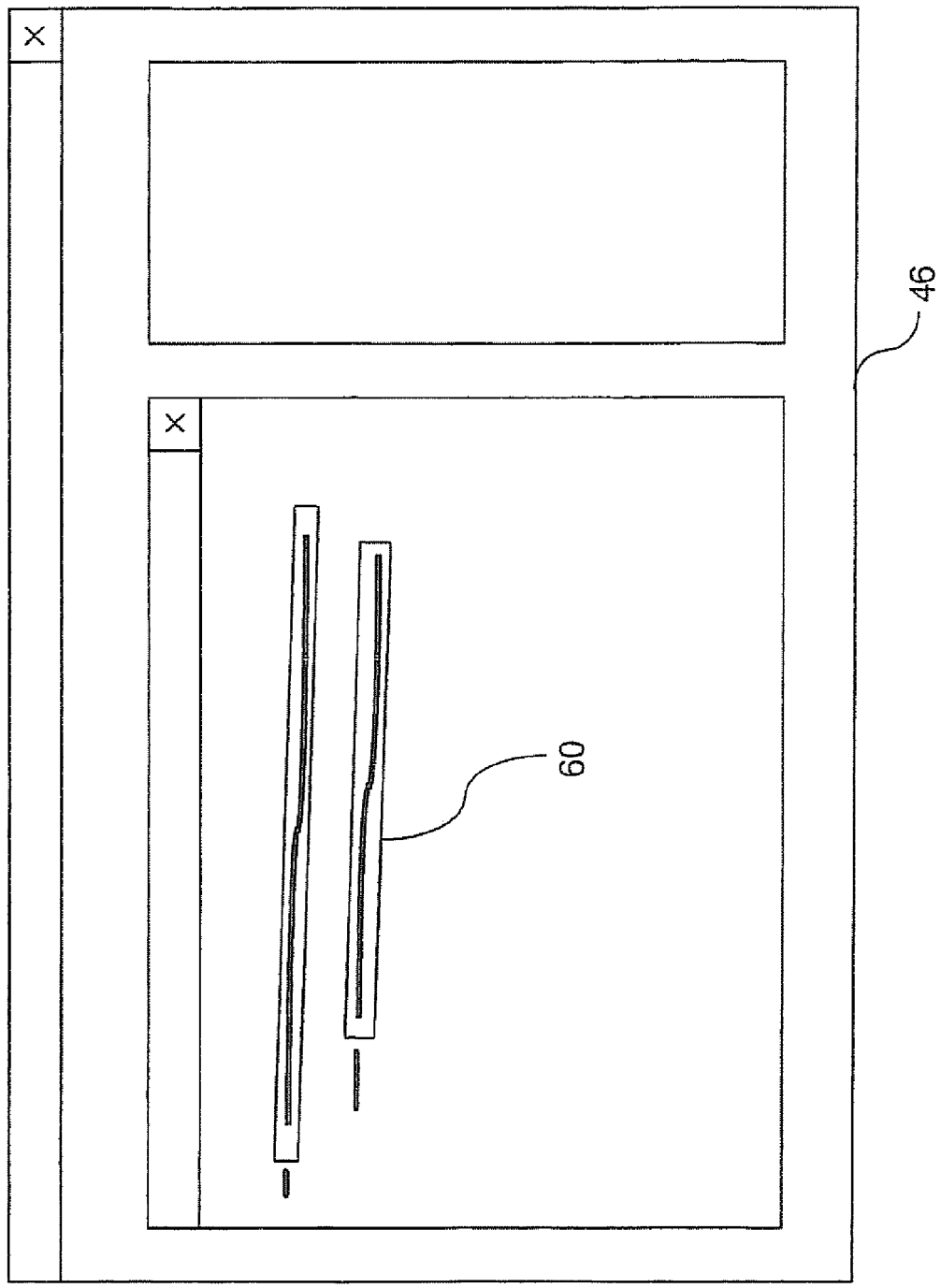
FIG. 4 is a screen shot of an interface showing the information obtained.
Figure 5:
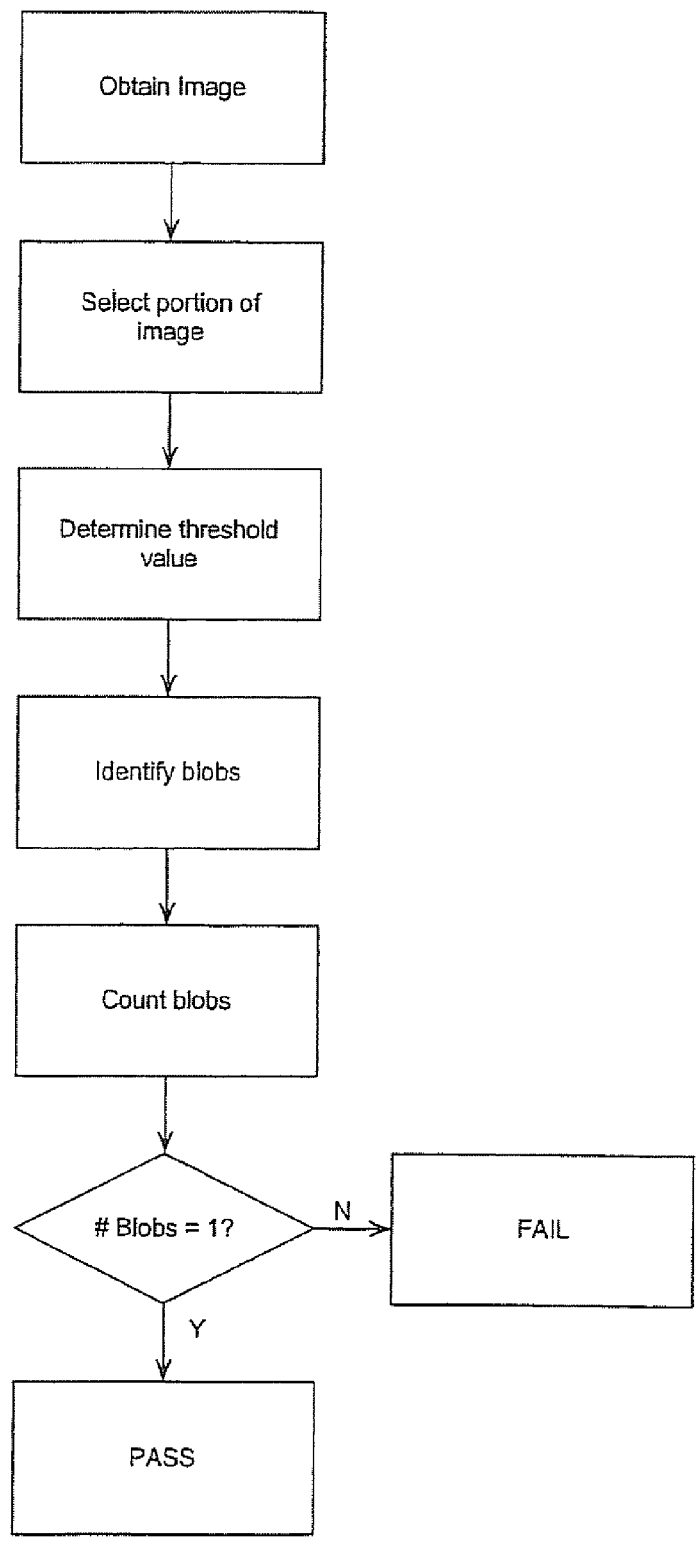
FIG. 5 is a flow chart indicating the processing of data obtained film the images shown in FIG. 4.

The signal processing is performed using selected procedures from commercially available imaging software such as that available from DVT Frameworks. As shown in FIGS. 4 and 5, after the image is captured, initially the region of interest is isolated by defining a window 60, and the distribution of the intensities associated with pixels within the defined window 60 is assessed. The windows may be preset in regions of the image where a plume is to be expected to facilitate automatic monitoring. Using the intensity distribution, a threshold to accord a light pixel versus a dark pixel is set. For example, those regions where scattering is present would be considered a light pixel and those where no scattering is present would be considered a dark pixel. Adjustment of the threshold may also accommodate different operating conditions, spray densities and distance from the camera 40.

Having established the threshold, the image is processed to look for regions of continuous brightness, typically referred to a "blobs". This can be performed using the blob tools available on the commercial software to identify a number of blobs present in the window 60. If there is a uniform distribution of spray along the sprayhead then a single blob would be detected indicating a continuous region of brightness from one end of the sprayhead 18 to the other as shown in FIG. 3(a) (i.e. the horizontal band 50). If however, there is a blocked nozzle or a reduced spray in certain areas, as shown in FIG. 3(b), then two or more blobs (e.g. 52 and 54 shown in FIG. 3(b)) will be identified indicating a discontinuity in the spray pattern 24. Similarly, if no blobs are observed then either the laser 30 is faulty or there is no spray. The detection of a plurality of blobs or no blobs can then be used to signal a fault and initiate remedial action.

It will be seen therefore that a simple monitoring of the propagation of the beam 32 in a spray pattern 24 formed by successive spray nozzles 22 provides an effective indication of the uniformity of the spray between separate nozzles 22, and allows the malfunction of a nozzle 22 to be detected and corrected. The identification may be done manually or may be used automated through image processing techniques that allow an claim to be initiated for corrective action. The imaging software is of course integrated with the spray control so that it is only responsive when the spray is to be delivered.

The system works best with a fine spray, as produced by an electrostatic sprayer (charging of the spray drops causes them to break up into finer drops than initially emitted from the nozzle), or other misting-type applicator.

The system functions best with a fine spray because the spray plume is "optically thin". This allows most of the light to pass through the plume and only a small fraction is scattered. Therefore a segment at the far end of the plume sees about the same light intensity, and scatters about the same fraction, as a plume segment near the beginning of the plume. The device may be used with other sprays with suitable compensation of the threshold to accommodate light absorption in the spray.

Although the invention has been described with reference to certain specific embodiments, various modifications thereof will be apparent to those skilled in the art without departing from the spirit and scope of the invention as outlined in the claims appended hereto.

What is claimed is:

1. A method of monitoring the application of a coating to a substrate from a plurality of nozzles spaced apart along at least one dimension of the substrate, the method comprising the steps of projecting a beam of coherent radiation horizontally through a spray of coating comprising overlapping spray patterns from said plurality of nozzles, said spray patterns overlapping between adjacent separate nozzles in said plurality of nozzles, obtaining an image of the beam as it propagates through said overlapping spray patterns and processing said image to identify a horizontal band in the image, the horizontal band representative of the beam as scattered by the spray, and determining discontinuities in the horizontal band in the image indicative of discontinuities of said overlapping spray patterns between separate nozzles.

2. A method according to claim 1 wherein discontinuities in the horizontal band in the image in excess of a predetermined value are utilized to identify discontinuities of said spray.

3. A method according to claim 1 wherein said beam of coherent radiation is a laser beam generated by a laser.

4. A method according to claim 3 wherein said laser includes a collimator to produce a non-Gaussian, substantially uniform intensity line from said laser beam.

5. A method according to claim 1 wherein said image is obtained by a camera, said camera transmitting said image to a computing device to perform said processing.

6. A method according to claim 5 wherein said computing device is connected to an interface, said interface permitting a user to interact with said image.

7. A method according to claim 1 wherein said image is obtained by a smart camera and said processing of said image occurs within said smart camera.

8. A method according to claim 1 wherein determination of said discontinuities in the horizontal band in the image triggers a step of initiating remedial action.

9. A method according to claim 1 wherein said plurality of nozzles are spaced along a plurality of sprayheads to produce a plurality of sprays, a beam of coherent radiation is projected through each spray, said image represents at least two of said beams, and said step of processing said image determines discontinuities in at least two horizontal bands in the image representing each of said at least two beams.

10. A method according to claim 1 wherein said processing comprises identifying blobs indicative of regions of continuous brightness in the horizontal band in the image, said method identifying a discontinuity by counting the number of said blobs wherein two or more blobs indicates at least one discontinuity.

11. A method according to claim 10 wherein said blobs are identified based on a predetermined threshold of said brightness, said threshold determined using an intensity distribution of said pixels.

* * * * *